(12) United States Patent
Berger et al.

(10) Patent No.: US 8,200,510 B1
(45) Date of Patent: *Jun. 12, 2012

(54) METHOD FOR SECURE DIAGNOSTIC SCREENING, SERVICING, TREATMENT, AND COMPLIANCE MONITORING FOR SLEEP APNEA FOR OPERATORS OF TRANSPORT VEHICLES

(75) Inventors: Mark Berger, Houston, TX (US); Helen Francis Berger, Houston, TX (US)

(73) Assignee: MK3SD, Ltd., Houston, TX (US)

( * ) Notice: Subject to any disclaimer, the term of this patent is extended or adjusted under 35 U.S.C. 154(b) by 581 days.

This patent is subject to a terminal disclaimer.

(21) Appl. No.: 12/509,251

(22) Filed: Jul. 24, 2009

Related U.S. Application Data

(63) Continuation-in-part of application No. 11/679,085, filed on Feb. 26, 2007.

(51) Int. Cl.
*G06Q 50/00* (2012.01)

(52) U.S. Cl. .......................................................... 705/3
(58) Field of Classification Search .................. 705/2–4
See application file for complete search history.

(56) References Cited

U.S. PATENT DOCUMENTS
6,811,538 B2 * 11/2004 Westbrook et al. ........... 600/529
* cited by examiner

*Primary Examiner* — Gerald J. O'Connor
*Assistant Examiner* — Mark Holcomb
(74) *Attorney, Agent, or Firm* — Buskop Law Group, PC; Wendy Buskop

(57) ABSTRACT

A secure method for delivering sleep apnea diagnostic services on an at least one operator of a transport vehicle to a transport company. The sleep apnea diagnostic services are delivered by a general coordinator using a system. The system includes at least one processor connected to an input device, an output device, and a data storage. The data storage includes a plurality of secure computer instruction. The processor is in encrypted communication with a network which is in encrypted communication with at least one client device.

25 Claims, 12 Drawing Sheets

Health Screening Survey
Step 1 of 3

Company Information
Company: [____100____] Operator #: [__102__]

Classification: [__104__] Location: [__106__]

Date of Hire: [____] ☐ ☐ YES, I am an applicant!
108

Personal Information
Last Name: [__110__] First Name: [__112__] MI: [114]

DOB: [____116____] SSN: [_____]
118

Sex: [__] Height: [____] Weight: [__] (lbs.)
120 122 124

[Continue to Step 2]

FIG. 3

Health screening survey
Step 2 of 3
For each question below, please choose the response that best fits your answer for that Question.

| Health information Question | Answers | |
|---|---|---|
| 1. Do you have high blood pressure? | ⊙ Yes ⊙ No | ⟵ 134 |
| 2. Do you have diabetes? | ⊙ Yes ⊙ No | ⟵ 136 |
| 3. Have you been treated for heartburn? | ⊙ Yes ⊙ No | ⟵ 138 |
| 4. Do you have heart problems? | ⊙ Yes ⊙ No | ⟵ 140 |
| 5. Have you ever undergone a heart operation or procedure? | ⊙ Yes ⊙ No | ⟵ 142 |
| 6. Do you take any of the following medications: isorbide dinitrate, Isordil, Ismo, nitroglycerin, amiadarone or Cardarone? | ⊙ Yes ⊙ No | ⟵ 144 |
| 7. Do you have sleep apnea? | ⊙ Yes ⊙ No | ⟵ 146 |
| 8. Do you take any of the following medications: Glucophage, Glucotrol, Actos or Avandia, or any other diabetes medications? | ⊙ Yes ⊙ No | ⟵ 148 |
| 9. Do you have COPD (emphysema)? | ⊙ Yes ⊙ No | ⟵ 150 |
| 10. Do you have asthma? | ⊙ Yes ⊙ No | ⟵ 152 |
| 11. Have you been treated for depression? | ⊙ Yes ⊙ No | ⟵ 154 |
| 12. Do you snore louder than talking? | ⊙ Yes ⊙ No | ⟵ 156 |
| 13. Does your snoring bother other people? | ⊙ Yes ⊙ No | ⟵ 158 |
| 14. Do you take any of the following medications: Plavix, Trental, or Persantine? | ⊙ Yes ⊙ No | ⟵ 160 |
| 15. Do you take ANY of the following medications: Protonix, Prevacid, Nexium, Pepcid, or Tagamet? | ⊙ Yes ⊙ No | ⟵ 162 |
| 16. On average, do you urinate more than once per night? | ⊙ Yes ⊙ No | ⟵ 164 |
| 17. Do you become drowsy while driving? | ⊙ Yes ⊙ No | ⟵ 166 |
| 18. Does head, back, neck, or joint pain affect your sleeping? | ⊙ Yes ⊙ No | ⟵ 168 |
| 19. Do you take any of the following medications: Vasotec, Cozar, Lotril, Norvasc, Enalapril, Lisinopril, Hydrolchlothiazide, or Lasix? | ⊙ Yes ⊙ No | ⟵ 169 |
| 20. Do you take any of the following medications: Inderal, Toprol, Metoprolol, Coreg, or Lopressor? | ⊙ Yes ⊙ No | ⟵ 170 |
| 21. Do you take any of the following medications: Digoxin, or Coumadin? | ⊙ Yes ⊙ No | ⟵ 172 |
| 22. Do you sleep restlessly or find the blankets on the floor in the morning? | ⊙ Yes ⊙ No | ⟵ 174 |
| 23. Has anyone noticed that you quit breathing during your sleep? | ⊙ Yes ⊙ No | ⟵ 176 |
| 24. Have you awakened from sleep with gasping breaths? | ⊙ Yes ⊙ No | ⟵ 178 |

[Continue to Step 3]

FIG. 4

Health Screening Survey
*Step 3 of 3*
*Situational Information*
Please indicate your chance of dozing under each of the following scenerios

| Situation | Chance of Dozing | | | |
|---|---|---|---|---|
| 1. Sitting and reading | ⊙ Never | ⊙ Slight | ⊙ Moderate | ⊙ High — 180 |
| 2. Watching TV | ⊙ Never | ⊙ Slight | ⊙ Moderate | ⊙ High — 182 |
| 3. Sitting inactive in a public place (e.g., a theater or meeting) | ⊙ Never | ⊙ Slight | ⊙ Moderate | ⊙ High — 184 |
| 4. As a passenger in a car for an hour without a break | ⊙ Never | ⊙ Slight | ⊙ Moderate | ⊙ High — 186 |
| 5. Lying down to rest anytime circumstances permit | ⊙ Never | ⊙ Slight | ⊙ Moderate | ⊙ High — 188 |
| 6. Sitting and talking to someone | ⊙ Never | ⊙ Slight | ⊙ Moderate | ⊙ High — 190 |
| 7. Sitting quietly after lunch without alcohol | ⊙ Never | ⊙ Slight | ⊙ Moderate | ⊙ High — 192 |
| 8. In a truck or car, while stopping for a few minutes in traffic | ⊙ Never | ⊙ Slight | ⊙ Moderate | ⊙ High — 194 |

*For Men Only!*
What is your neck size? ☐ — 195

[ Submit Survey ]

*FIG. 5*

Health Screening Survey

Thank you, USER NAME!
We appreciate your taking the time to complete this health screening survey. Your information has been securely processed, and as with all personal medical records, will be kept confidential.

*FIG. 6*

Example Company Health Screening Survey Rankings

You currently have a total of 86 survey respondents, which have been broken down into six categories based on sex, WA (Witnessed Apnea), and EDS (Excessive Daytime Sleepiness).

Respondents — 198

| Sex | WA+ | EDS+ / WA- | EDS- / WA- |
|---|---|---|---|
| Male | 26 | 5 | 44 |
| Female | 2 | 1 | 8 |

Find a Survey

SSN: ☐☐ ☐ [Find]
Operator #: ☐ [Find]
Last Name: ☐ [Find]

There are currently 14 respondents that have been marked for immediate contact due to self-admitted Sleep Apnea. To view a complete list, click here.

To review survey respondents based on more specific criteria, click here for additional reporting tools.

[Return to Main Menu]

FIG. 7

Example Company Survey Respondents: Sleep Apnea Alert!

| | Name / SSN | Location | Operator # | Sex | WA± | Probability | Alert | Date | Date of Hire | Status |
|---|---|---|---|---|---|---|---|---|---|---|
| 1. | Berger, Mark B<br>123-45-6711 | Location A | 007 | Male | ⊕ | 1.000 | 🔔 | 3/27/2006 | 3/27/2005 | |
| 2. | berger, mark b<br>222-22-222 | Location B | 123 | Male | ⊕ | 1.000 | 🔔 | 2/13/2007 | 2/13/2005 | |
| 3. | Green, Paul<br>123-45-6711 | Location B | 00000 | Male | ⊕ | 1.000 | 🔔 | 2/15/2006 | 2/15/2005 | |
| 4. | Michael, Johnson<br>999-8897766 | Location A | 000066 | Male | ○ | 1.000 | 🔔 | 11/15/2006 | 11/15/2005 | |
| 5. | Smith, James<br>123-45-6776 | Location A | abc123 | Male | ⊕ | 1.000 | 🔔 | 11/22/2006 | 11/22/2005 | |
| 6. | Test, Test T.<br>111-11-1111 | Location A | 111111 | Male | ⊕ | 1.000 | 🔔 | 2/16/2007 | 2/16/2005 | |
| 7. | O'Grady, John<br>123-45-6711 | Location B | 00000 | Male | ○ | 0.594 | 🔔 | 2/15/2006 | 2/15/2005 | ✉ 📧 |
| 8. | Gordon, John | Location A | 00000 | Male | ○ | 1.000 | 🔔 | 2/15/2006 | 2/15/2005 | |
| 9. | Fills, Christopher | Location B | 00000 | Male | ⊕ | 0.666 | 🔔 | 2/15/2006 | 2/15/2005 | |
| 10. | Turk, Larry | Location A | 00000 | Male | ⊕ | 0.985 | 🔔 | 2/15/2006 | 2/15/2005 | ✉ 📧 ⓘ |
| 11. | Brady, Kim | Location B | 00000 | Female | ○ | 0.000 | 🔔 | 2/15/2006 | 2/15/2005 | ✉ 📧 ⓘ |

Download Report

FIG. 8

Health Screening Survey Results: Berger, Mark B.

Personal Information

- 232 — Name: Berger, Mark B. [Change] — 249
- 234 — SSN: 123-45-7-6711
- Company: Example Company [Change] — 249
- Classification: N/A
- 236 — Location: Location A [Change] — 249
- 238 — Operator #: 007 [Change] — 249
- Applicant: No
- 240 — Sex: Male
- Age: 51 yrs. (DOB 4/15/1956)
- Height: 5' 11"
- Weight: 213 (lbs.)

Comments (Edit) — 251

[Delete Survey]

Scoring — 246

Probability Score: 1.000
WA ⊕ EDS ⊕ BMI: 29.7 — 245
244

248 — This user has been flagged for a Sleep Apnea Follow-up call!

[Remove Apnea Flag]

Sleep Test
This individual has no available test results.

Follow Up
There has been no follow-up with this individual.

[Modify]

*FIG. 9A*

Complete List of Survey Responses (Recorded on 3/27/2006)

Health Information

| | |
|---|---|
| 1. Do you have high blood pressure? | Yes |
| 2. Do you have diabetes? | Yes |
| 3. Have you been treated for heartburn? | Yes |
| 4. Do you have heart problems? | No |
| 5. Have you ever undergone a heart operation or procedure? | No |
| 6. Do you take ANY of the following medications: Isordil, Ismo, nitroglycerin, Cardarone, or Amiodarone? | No |
| 7. Do you have sleep apnea? | Yes |
| 8. Do you take ANY of the following medications: Glucophage, Glucotrol, Actos, or Avandia, or any other diabetes medications? | Yes |
| 9. Do you have COPD (emphysema)? | No |
| 10. Do you have asthma? | No |
| 11. Have you been treated for depression? | No |
| 12. Do you snore louder than talking? | Yes |
| 13. Does your snoring bother other people? | No |
| 14. Do you take ANY of the following medications: Plavix, Trental, or Persantine? | No |

Epworth Information

| | |
|---|---|
| 1. Sitting and reading | Never |
| 2. Watching TV | Never |
| 3. Sitting inactive in a public place (e.g., a theater or meeting) | Never |
| 4. As a passenger in a car for an hour without a break | High |
| 5. Lying down to rest anytime circumstances permit | Moderate |
| 6. Sitting and talking to someone | Slight |
| 7. Sitting quietly after lunch without alcohol | Never |
| 8. In a truck or car, while stopping for a few minutes in traffic | Never |

Sex-Specific Information

What is your neck size?

*FIG. 9B*

Complete List of Survey Responses (Recorded on 3/27/2006)
Health Information

15. Do you take ANY of the following medications:
    Protonix, Prevacid, Nexium, Pepcid, or Tagamet? — No
16. On average, do you urinate more than once per night? — No
17. Do you become drowsy while driving? — Sometimes
18. Does head, back, neck, or joint pain affect your sleeping? — Yes
19. Do you take ANY of the following medications:
    Vasotec, Cozar, Lotril, Norvasc, Enalapril, Lisinopril,
    Hydrochlorthiazide, or Lasix? — Yes
20. Do you take ANY of the following medications:
    Inderal, Toprol, Metoprolol, Coreg, Lopressor? — No
21. Do you take ANY of the following medications:
    Digoxin, Coumadin? — Yes
22. Do you sleep restlessly or find the blankets on
    the floor in the morning? — Yes
23. Has anyone noticed that you quit breathing during
    your sleep? — No
24. Have you awakened from sleep with gasping breaths? — Yes

Screening History

| | Date | BMI | WA ± | Probability | Alert | Status |
|---|---|---|---|---|---|---|
| 1. | 3/27/2006 | 29.7 | ⊕ | 1.000 | 🚩 | |

*FIG. 9C*

Example Company Survey Respondents: Female / EDS- / WA-
Filter/Sort Options

Classification: <All Classifications> ▼    Location: <All Locations> ▼    Treatment Facility: <All Facilities> ▼    Download Report Sort by: Risk ▼ Desc. ▼    Then by: Date of Entry ▼ Desc. ▼    Apply Filter

26 Result(s) found                                                                                     <Previous   Page 1 of 1

| Name | SSN | Location | Operator # | Sex | WA± | Probability | Alert | Date | Date of Hire | Status |
|---|---|---|---|---|---|---|---|---|---|---|
| 1. Bama, John | | Location A | 00000 | Male | ⊕ | 1.000 | | 3/27/2006 | 3/27/2005 | |
| 2. Berger, Mark B | 123-45-6711 | Location A | 007 | Male | ⊕ | 1.000 | 📜 | 3/27/2006 | 3/27/2005 | |
| 3. berger, mark b | 222-22-222 | Location B | 123 | Male | ⊕ | 1.000 | | 2/13/2007 | 2/13/2005 | |
| 4. Elk, Christopher | | Location A | 00000 | Male | ⊕ | 1.000 | 📜 | 2/15/2006 | 2/15/2005 | |
| 5. Green, Paul | | Location B | 00000 | Male | ⊕ | 1.000 | 📜 | 11/15/2006 | 11/15/2005 | |
| 6. Lincoln, Larry | 666-55-4444 | Location A | 00000 | Male | ⊕ | 1.000 | | 11/22/2006 | 11/22/2005 | |

*FIG. 10*

METHOD FOR SECURE DIAGNOSTIC SCREENING, SERVICING, TREATMENT, AND COMPLIANCE MONITORING FOR SLEEP APNEA FOR OPERATORS OF TRANSPORT VEHICLES

CROSS-REFERENCE TO RELATED APPLICATIONS

The present application is a Continuation-in-Part of U.S. patent application Ser. No. 11/679,085, filed on Feb. 26, 2007; entitled "Method for Secure Diagnostic Screening, Servicing, Treatment and Compliance Monitoring for Sleep Apnea in Truck Drivers", which is incorporated in its entirety by reference.

FIELD

The present embodiments generally relate to a secure method for providing sleep apnea diagnostic services on at least one operator for at least one transportation vehicle.

BACKGROUND

Sleep apnea is very common, particularly in the operator of a transport vehicle population. Studies show that up to 28 percent of operator of a transport vehicles may be afflicted. Primary risk factors include being male, overweight, and over the age of forty. Fortunately sleep apnea can be diagnosed and, with treatment, quality of life and health benefits can be realized.

Sleep apnea is defined as the cessation of breathing during sleep. Obstructive sleep apnea (OSA) is the most common form of sleep apnea. OSA occurs when the tissues in the back of the throat repetitively collapse during sleep, producing snoring and complete airway blockage. This blockage creates pauses in breathing that occur repeatedly every night. In severe cases they can occur as frequently as every 30 seconds. Alarmingly, they can last up to a full minute.

These repetitive pauses in breathing during sleep are accompanied by a reduction in blood oxygen levels and are followed by an arousal response. This response includes a release of substances into the bloodstream, which promote elevation of blood pressure, inflammation, insulin resistance, and a disruption of the brain wave sleep pattern. The consequences of untreated sleep apnea include poor quality sleep, excessive daytime fatigue and sleepiness, irritability, hard-to-control high blood pressure and diabetes, heart disease, and stroke. Interestingly and not coincidentally, many of these same medical conditions account for the majority of health-related expenditures in the operator of a transport vehicle population. Moreover, untreated sleep apnea may be responsible for job impairment and motor vehicle crashes.

Traditional methods for diagnosing sleep apnea in airline captains and ship captains are time consuming and often interfere with the ability to perform their routes, which results in the transport company, as well as the transportation driver suffering economic deprivation.

The recognition of the dangers associated with commercial transportation operators and improper sleep is evident in the numerous regulations developed to ensure that commercial transport device operators receive proper sleep. For example, restrictions on the number of hours an operator of a transportation vehicle can drive in a day have been implemented to prevent operators from driving a vessel, such as a floating vessel without proper sleep.

There exists a need to efficiently screen for sleep apnea in operators of various types of transportation vehicles.

There exists a need to efficiently determine whether an operator of a commercial vehicle has sleep apnea.

There exists a need to efficiently treat those with sleep apnea.

There exists a need to efficiently monitor an operator of a transport vehicles use of sleep apnea treatment equipment.

The present embodiments meet these needs.

BRIEF DESCRIPTION OF THE DRAWINGS

The detailed description will be better understood in conjunction with the accompanying drawings as follows:

FIG. 3 shows an example sleep apnea diagnostic screening questionnaire requesting company personal information and individual personal information usable with the embodiments of this method.

FIG. 4 shows an example sleep apnea diagnostic screening questionnaire requesting health information usable with the embodiments of this method.

FIG. 5 shows an example sleep apnea diagnostic screening questionnaire requesting situational answers from a situational questionnaire usable with the embodiments of this method.

FIG. 6 shows an example of a thank you screen that is shown after completing the health screening survey usable with the embodiments of this method.

FIG. 7 shows an example screen of survey rankings of how a general coordinator would view operator of a transport vehicles after they had completed the health screening survey usable with the embodiments of this method.

FIG. 8 shows an example of survey rankings usable with the embodiments of this method.

FIGS. 9A, 9B, and 9C show screens of an operator of a commercial transport vehicle after a general coordinator had selected the operator and the operator's answers to the health screening questions usable with the embodiments of this method.

FIG. 10 shows the ability of a general coordinator to filter between different operators of transport vehicles that are in the database usable with the embodiments of this method.

Figure 1:
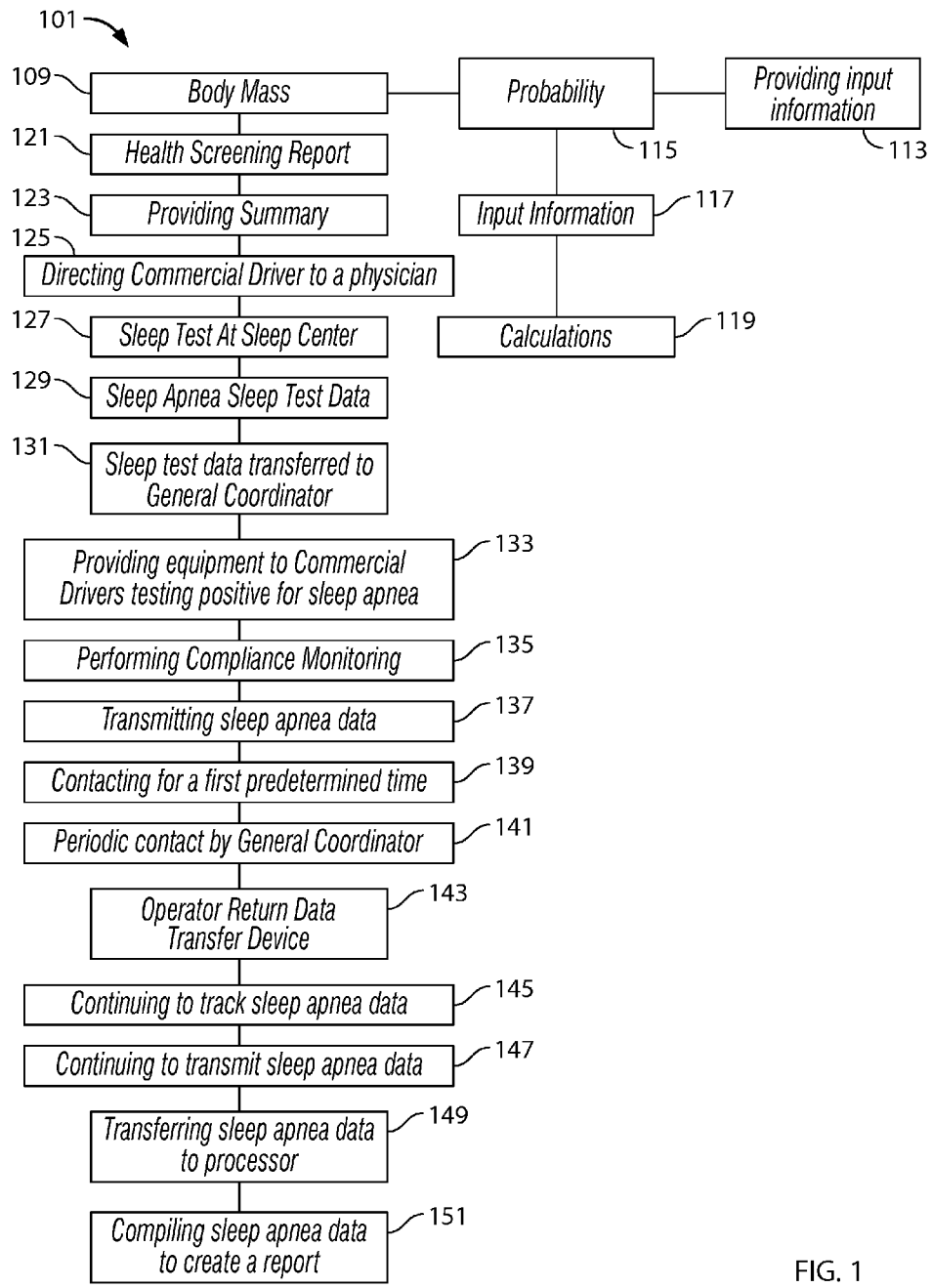
FIG. 1 depicts a general flow diagram of an embodiment of the method.

The present embodiments are detailed below with reference to the listed Figures.

DETAILED DESCRIPTION OF THE EMBODIMENTS

Before explaining the present method in detail, it is to be understood that the method is not limited to the particular embodiments and that they can be practiced or carried out in various ways.

The embodiments relate to a secure method for a general coordinator to deliver sleep apnea screening, sleep apnea treatment and sleep apnea compliance monitoring on at least one operator of a transport vehicle for a transport company, such as an airline or a cruise line.

The method includes the step of the operator of a transport vehicle providing input information to the general coordinator such as with software on a computer with computer instructions in data storage that provides questions to the operator enabling them to enter the answers to data storage of the computer. The operator of a transport vehicle provides input information to the general coordinator by completing a secured sleep apnea diagnostic screening questionnaire and storing the answers in data storage of the computer, which can be linked to another data storage through a network.

The secured sleep apnea diagnostic screening questionnaire can request information relating to the transport operator's employee information; the operator of a transport vehicle's individual personal information, such as his age; the operator of a transport vehicle's personal health information, such as history of high blood pressure; and similar information pertinent to operator of a transport vehicle that can be used to screen for sleep apnea.

It can be contemplated that the personal information can include information such as the operator of a transport vehicle's name, an employee number for each operator of a transport vehicle, such as 12345; gender for each operator of a transport vehicle; social security number for each operator of a transport vehicle, such as 123-45-6078; an alert icon for self admitted sleep apnea; date of input of information; date of hire; or at least one designed field identified by the transport company.

Additionally the secured sleep apnea questionnaire can include a situational questionnaire which can include gender related questions, such as neck circumference, or menopausal status. Many of the questions can be used in order to indirectly determine sleep apnea conditions.

In an embodiment of the method, the input information can be provided to the general coordinator by the operator of a transport vehicle using a client device to provide answers to the sleep apnea screening questionnaire to the general coordinator. The client device can be a computer, a personal digital assistant, a cell phone, an iPhone™ or a similar device. The client device can be in encrypted communication with a network.

The network is in communication with at least one server with a processor, data storage and computer instructions in the data storage for instructing the processor to communicate with the network. The server communicates with an input device, an output device, and the data storage.

The data storage can include encrypted computer instruction for the secure sleep apnea screening questionnaire, and encrypted computer instructions for providing a confirmation, such as e-mail to the operator of a transport vehicle.

The confirmation, if an email, an instant message, or a similar confirmation, can inform the operator of a transport vehicle of the answers provided to the sleep apnea screening questionnaire, and inform the operator of the transport vehicle that the information provided in the sleep apnea screening questionnaire is secure and complete.

It can be further contemplated that the confirmation, such as the e-mail, can include an interpretation of the sleep apnea screening questionnaire, such as an individualized health screening report. For example, the confirmation will inform the operator of a transport vehicle that he is at high risk for sleep apnea and should be tested for sleep apnea.

The general coordinator determines positive predictive values for sleep apnea by categorizing the input information. The general coordinator can use the computer instructions stored in the data storage of the server to categorize the input information.

The input information can be categorized into the following: male Witnessed Apnea Positive WA+), female Witnessed Apnea Positive WA+), male Witnessed Apnea Negative WA-) and Excessive Daytime Sleepiness Positive EDS+), female Witnessed Apnea Negative WA-) and Excessive Daytime Sleepiness Positive EDS+), male Witnessed Apnea Negative WA-) and Excessive Daytime Sleepiness Negative EDS-), or female Witnessed Apnea Negative WA-) and Excessive Daytime Sleepiness Negative EDS-).

The input information categorized into male WA- and EDS+, require an odds ratio calculation in combination with a liner regression model to determine the predictive value for sleep apnea for each of the operator of a transport vehicles associated with the input information in the groups male WA- and EDS+, female WA- and EDS+.

The input information in the category of male WA- and EDS-, or female WA- and EDS-, and female WA- and EDS+ requires an odds ratio calculation to determine the predictive value of sleep apnea for the operator of a transport vehicles associated with the input information associated with the input information categorized into the male WA- and EDS-,female WA- and EDS-, and female WA- and EDS+.

The general coordinator can additionally calculate the body mass index for each operator of a transport vehicle.

The embodiments of the method can further include the step wherein the general coordinator provides a health screening service report using the categorized input information to the transport company.

The health screening report is adapted to identify a plurality of operators of transport vehicles with high predictive values for sleep apnea for management by the transport company.

The health screening service report can include a rating of individualized numerical scores indicating a positive predictive value, and a high, medium, or low positive predictive value.

The positive predictive values can be indicated by a red, yellow, or green flag indicating high, intermediate, or low risk for sleep apnea, respectively. It can be contemplated that colors alone can be used without any specific icon to indicate high, medium, or low positive predictive values. It is also contemplated that textual words, high, medium, and low can be used to indicate high, medium, or low positive predictive values in another embodiment.

The health screening service report can include the transport company's name; the sex of the operator of a transport vehicle; the presence or absence of sleep apnea; the operator of a transport vehicle's body mass index, the neck size range of the operator of a transport vehicle and other physical indicia that may not lead the operator to think they are being asked questions to determine if they have sleep apnea.

It can further be contemplated that the health screening service report can include questions for the operator to admit that the operator has hypertension; diabetes; heart disease; lung disease; asthma; heart burn; or frequent urination at night any of which, in combination with sleep apnea can be a significant problem or a symptom of a physical problem.

Further, the health screening service report can include a look-up table for each operator of all the transport vehicles in a fleet of transport vehicles. The look-up table can be organized using all of the operators' employee numbers, or social security numbers or some other personal identification code.

The operators of transport vehicles with high predictive values for sleep apnea are directed to go to a physician to obtain a prescription for a sleep apnea sleep test as the next step.

A sleep apnea sleep test can then be performed on the operator in a sleep center to obtain sleep apnea sleep test data.

The sleep apnea sleep test data can then be transmitted to the general coordinator.

The sleep apnea sleep test data can be entered into the data storage of the computer and then using computer instruction, such as a linear regression model, the sleep apnea test data along with the questions of the questionnaire are together analyzed to determine which of the operators have sleep apnea.

The transmission from the sleep center physician to the general coordinator can be by e-mail, fax, post, courier, or another fast and confidential manner.

The general coordinator provides sleep apnea treatment equipment to the operator of a transport vehicle with sleep apnea simultaneously with the conclusion of the sleep apnea sleep test.

Providing the sleep apnea treatment equipment to the operator of a transport vehicle simultaneously with the conclusion of the sleep apnea sleep test is an improvement over traditional methods for treating sleep apnea which have time delays.

With traditional methods for treating sleep apnea, the time delay between the test and providing the equipment to a person in need, it can take several days or weeks. With this method the drivers can rest better, and accordingly, cause fewer accidents, and be better prepared for emergency situations which may involve saving lives by quick action, rather than lethargic, sleep deprived behavior.

The delay in the operator receiving the sleep apnea treatment equipment can delay the operator of a transport vehicle's deliveries and cost the company significant revenue.

The delay in the operator of obtaining the equipment, such as a continuous positive airway pressure (CPAP) machine, can be a great cost to the operator of a transport vehicle, they could get into an accident or be laid off until they have the equipment, which includes monitoring equipment, verifying that the sleep apnea equipment, such as a CPAP machine is used.

The cost associated with the delays in the operator of a transport vehicle's deliveries has traditionally prevented transport companies from seeking sleep apnea treatment for operators of a transport vehicles.

By simultaneously providing the sleep apnea treatment equipment to the operator of transport vehicles with sleep apnea at the conclusion of the sleep apnea sleep test the delay in the operator of a transport vehicle's deliveries is eliminated and safety is improved.

The sleep apnea treatment is typically with a continuous positive airway pressure CPAP machine which uses a compliance chip for monitoring the usage and efficacy of the sleep apnea treatment equipment. A data transfer device can be paired with the CPAP machine for transmitting the monitoring data to a database formed in data storage of a computer of the general coordinator, which can be located in the human relations department of a company, such as a work boat company, or a fast ferry company.

The method includes the step of the general coordinator performing compliance monitoring on the operator of a transport vehicles that tested positive for sleep apnea. The operator of a transport vehicle with sleep apnea uses the CPAP machine and the data transfer device to transmit sleep apnea treatment equipment data from the sleep apnea treatment equipment, such as the CPAP machine, to the general coordinator.

The sleep apnea treatment equipment data can include data, such as mask leakage, hours of use, and an apnea index based on throat closure during CPAP machine treatment.

The data transfer device is adapted for use with a data transfer system, such as a beeper data transfer system, a cell phone data transfer system, a hardwired system, or a wireless data transfer system. The data transfer system is adapted to transmit sleep apnea treatment equipment data from the data transfer device to the general coordinator in an embodiment, on a 24/7 continuous basis for continuous feed to the general coordinator from multiple operators simultaneously.

It can be contemplated that an executive dashboard could be used by the general coordinator to monitor usage of the treatment machines, and the results synchronously and continuously to have a continual awareness of the heath status of the operators of the transport vehicles relative to the sleep apnea.

An embodiment of the method further includes the step of the general coordinator contacting each operator of a transport vehicle with sleep apnea after a first predetermined period of continuous compliance monitoring.

During this first contact, the general coordinator ascertains sleep apnea treatment equipment performance from the operator. The general coordinator at this time can conduct trouble shooting to make sure that there is optimal performance of the CPAP machine, and the other sleep apnea treatment equipment. The first predetermined time of compliance monitoring can be for a range between 2 days to 3 days.

The general coordinator asks the operator of a transport vehicle during the first contact if the mask is fitting fine and/or if the mask is leaking. If the operator of a transport vehicle indicates that the mask is leaking the general coordinator can recommended various actions that can remedy the leaking mask, such as tightening the mask, loosening the mask, adjusting the position of the mask and/or connecting hose, or suggesting a different type of mask with a seal more appropriate to the facial structure of the operator of the transport vehicle.

The general coordinator contacts each transport vehicle operator periodically following the first predetermined period of continuous compliance monitoring. The periodic contact can be weekly or bi weekly or monthly.

After a second predetermined time, the individual operator of a transport vehicle with sleep apnea can return the data transfer devices to the general coordinator. The second predetermined time of continuous compliance monitoring can be for a period of time ranging between about 2 weeks to about 4 weeks.

It can be contemplated that the general coordinator can continue to track sleep apnea treatment equipment data for each operator of a transport vehicle, by using data transmitted from the compliance chip installed in the CPAP machine. The data transmission can be over a network, such as a wireless network.

The method can contemplate that the general coordinator continues to track sleep apnea treatment equipment data for each of the operator of a transport vehicles with sleep apnea simultaneously or sequentially or by a "snapshot" technique, of selective sampling of the monitored data.

When each operator of a transport vehicle with sleep apnea downloads the sleep apnea treatment equipment data, the data is encrypted to a removable data storage device.

After the operator of a transport vehicle with sleep apnea downloads the sleep apnea treatment equipment data, the general coordinator transfers the sleep apnea treatment equipment data from the encrypted removable data storage device to a processor. The transferred sleep apnea treatment equipment data from the encrypted removable data storage device to processor can include between 2 months to 4 months of sleep apnea treatment equipment data but it can include data from shorter periods of time or longer periods of time, such as 6 months or even a year, and as short ads two days.

It can be contemplated that the encrypted removable data storage device can be a flash memory chip, a flash drive, a portable hard drive, a modem, a direct cable connection to a processor, such as a data card from ResMed™ or a removable data storage device from Respironics™.

The general coordinator can compile the sleep apnea treatment equipment data using the processor and a linear regression model, or a set of algorithms which enable the data to be categorized to have high, medium and low predictor values.

Additionally, the general coordinator can generate a sleep apnea treatment compliance status report. The general coordinator can provide the compliance status report for each operator of a transport vehicle to the appropriate transport company, such as a train company like the Burlington Northern Sante Fe Company that operates equipment through Texas.

It can further be contemplated that an embodiment of the method includes delivering sleep apnea screening information, sleep apnea treatment which can include pills, and sleep apnea treatment compliance monitoring, simultaneously to a plurality of operators of a transport vehicles in a plurality of transport companies.

The method in an embodiment performs screening for sleep apnea, treatment for sleep apnea, and compliance monitoring of sleep apnea all within a few days of each activity occurring, such as 5 days, thus contributing to a reduced risk for potentially dangerous vehicular accidents, such as airplane accidents, boating accidents, or train accidents, thereby preventing costly loss or damage of equipment, loss of time, preventing injury, and saving lives.

Treated sleep apnea has also been shown to improve an individual's health through better control of blood pressure and diabetes, by identifying and treating blood pressure and diabetes, and reducing the risk for heart attacks and stroke by identifying symptoms and other indicators quickly and easily, without the operator really knowing that the questions being answered are yielding such results.

It can be contemplated that the method can also include creating reports for the general manager of the program or from the companies using the program on a plurality of their operators simultaneously.

The reports can not only provide the sleep test data, and scores, as well as physical characteristics of the operator and symptoms of the operators for conditions other than sleep apnea, but can be provide a report with information verifying delivery of sleep apnea equipment.

An alternative embodiment of the method can further include the step of confirming the transport company has a United States Health Insurance Portability and Accountability Act HIPAA) of 2002, 42 C.F.R. §164, compliant release for each operator of a transport vehicle.

It is contemplated that the present method can be compliant under the United States Health Insurance Portability and Accountability Act (HIPAA) of 1996, the final regulation of the HIPAA privacy rule of December 2000, and the Final Rule modifications of August 2002. It is further contemplated that any protected health information (PHI) obtained using the present method can be de-identified when stored and processed to further comply with the requirements of HIPAA.

FIG. 1 is a flow diagram for an embodiment of the method for identifying sleep apnea in a plurality of operators of transport vehicles, by performing sleep apnea screening, sleep apnea treatment, and sleep apnea treatment compliance monitoring on an at least one operator of a transport vehicle to a transport company by a general coordinator see the step identified as element 101. The transport company can be a commercial transport company, an interstate intermodal transport company, or a intrastate transport company, a cruise line, a work boat company, a taxi company, an air charter fleet, a cruise line, a dinner cruise fleet, a fishing fleet, a helicopter fleet or similar fleets of transport vehicles, including but not limited to towboats on the inter-coastal waterway.

The general coordinator can be a doctor, health clinic, healthcare network, or a provider of sleep apnea-related services in the human relations department of a company providing transport vehicles. The general coordinator coordinates with the physician and a third party vendor, such as a manufacturer of CPAP machines and related equipment supplying sleep apnea treatment equipment.

FIG. 1 shows the operator of a transport vehicle providing input information to the general coordinator using a sleep apnea diagnostic screening questionnaire 113. For example, the operator of a transport vehicle can go to the transport company's office and complete the sleep apnea diagnostic screening questionnaire by hand and turn the form into the general coordinator. Alternatively, the process is computer assisted completion of the questionnaire.

Figure 2:
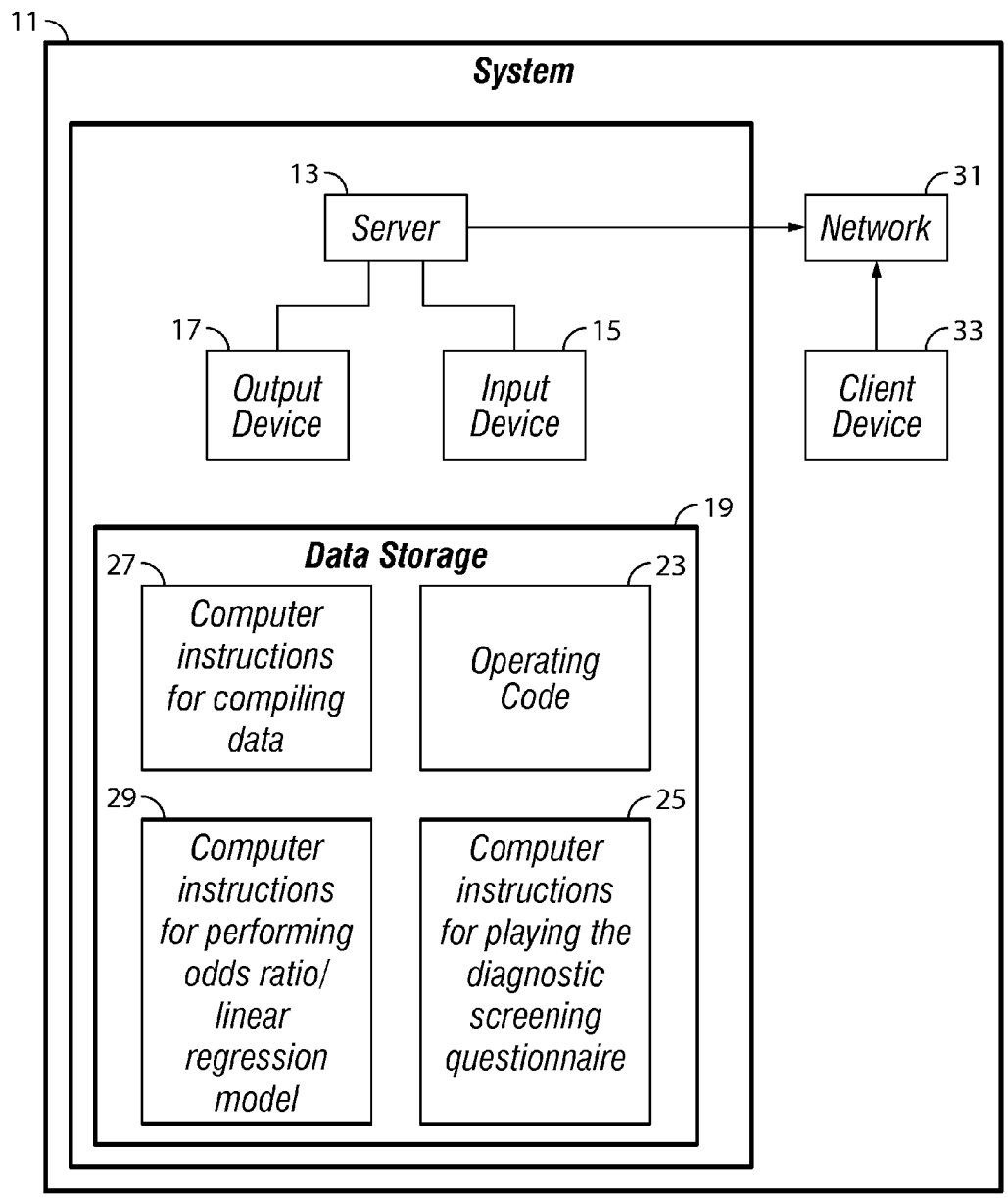
FIG. 2 depicts a system usable with the embodiments of the method.

If the method is to be computer assisted, the general coordinator would use a system akin to the one depicted in FIG. 2.

FIG. 2 shows a method which allows the operator of a transport vehicle to electronically fill out the sleep apnea diagnostic screening questionnaire using a network, such as the internet, a WAN line, a local area network, and similar communication networks from a desk top computer or a lap top or even a cell phone.

The network is in communication with the client device, which can be a lightweight laptop personal computer.

After the sleep apnea diagnostic screening questionnaire is completed, the general coordinator determines positive predictive values for sleep apnea of each operator of a transport vehicle of the company.

The determination of the positive predictive values is indicated as probability 115. The input information is categorized. The input information 117 is analyzed using associated calculations 119. The input information 117 is categorized using secured input instructions on a server.

The input information can be categorized into the following: male Witnessed Apnea Positive WA+), female Witnessed Apnea Positive WA+), male Witnessed Apnea Negative WA−) and Excessive Daytime Sleepiness Positive EDS+), female Witnessed Apnea Negative WA−) and Excessive Daytime Sleepiness Positive EDS+), male Witnessed Apnea Negative WA−) and Excessive Daytime Sleepiness Negative EDS−), or female Witnessed Apnea Negative WA−) and Excessive Daytime Sleepiness Negative EDS−).

The input information categorized into male WA− and EDS+, requires an odds ratio calculation in combination with a liner regression model to determine the positive predictive value for sleep apnea for each of the operator of a transport vehicles associated with the input information in the groups male WA− and EDS+.

The input information in the category of male WA− and EDS−, female WA− and EDS−, and female WA− and EDS+ requires an odds ratio calculation to determine the positive predictive value of sleep apnea for the operator of a transport vehicles associated with the input information associated with the input information categorized into the male WA− and EDS−, female WA− and EDS, and female WA− and EDS+.

The general coordinator can also make a calculation of the body mass index for each operator of a transport vehicle 109. The calculation is usually performed simultaneously when the general coordinator determines that the operator of a transport vehicle has a probability 115 for sleep apnea.

The next step is providing a health screening service report 121. The general coordinator provides the health screening service report to the transport company. The health screening service report can identify each operator of a transport vehicle with high predictive values for sleep apnea. In this embodiment of the method the general coordinator provide a summary of all positive predictive values using input information to the transport company 123, such as a listing of the probabilities of sleep apnea.

For example, the health screening service report can indicate that an operator of a transport vehicle has inputted data into the sleep apnea diagnostic screening questionnaire that indicates a high likelihood of sleep apnea and the report then recommends that the operator of the transport vehicle, such as a bus driver, or ferry captain, receive a sleep apnea sleep test.

In an alternative embodiment, the health screening report indicates that the data inputted into the sleep apnea diagnostic screening questionnaire indicates that the operator of a transport vehicle has a low predictive value for sleep apnea and that he does not need to receive a sleep apnea sleep test.

As a subsequent step, the operator of a transport vehicle with high predictive values for sleep apnea is directed to go to a physician to obtain a prescription for a sleep apnea sleep test 125.

Once the operator of the transport vehicle, such as an airline pilot, with sleep apnea receives a prescription to undergo a sleep apnea sleep test, then the operator takes the sleep apnea sleep test at a sleep center 127, provided the operator has a high predictive value, such as an 80 percent to 90 percent positive predictive value.

The sleep apnea sleep test can be performed for one night to obtain sleep apnea sleep test data 129, such as data on an amount of time asleep, data recording EEG stages of sleep, data related to the number of respiratory events that occur while asleep, blood oxygen levels while asleep, and leg movements present while asleep.

Next, the physician transmits the sleep apnea sleep test data to the general coordinator 131.

The transmission of the sleep test data 131 can be by electronic transfer, written transmission, or verbal transmission by using traditional means of communication, such as fax, e-mail, or a telephone.

The sleep apnea sleep test can be conducted at a free-standing sleep diagnostic facility, a hospital-based sleep diagnostic facility, or an un-attended home sleep diagnostic protocol.

After the sleep apnea sleep test, the general coordinator provides sleep apnea treatment equipment to the operator of a transport vehicle that has tested positive for sleep apnea 133.

The sleep apnea treatment equipment has a data transfer device paired with a CPAP machine and related equipment such as masks. The CPAP machine has a compliance chip resident in the CPAP machine to monitor hours of usage, mask leakage, and apnea index. The sleep apnea treatment equipment is supplied simultaneously with the conclusion of the sleep apnea sleep test.

Subsequent to providing sleep apnea treatment equipment to the operator of a transport vehicle having sleep apnea, the general coordinator performs compliance monitoring on all of the operators of transport vehicles that have sleep apnea 135.

A receipt can be scanned and uploaded into the files of the pilot, captain, bus drive, train engineer, or other transportation operator and provided to the airline, shipping company, train company, cruise line or other company for which the operator is working to enable tracking of the equipment provided to the operator of a transport vehicle.

The operator of the transport vehicle transmits sleep apnea treatment equipment data, such as the CPAP machine's performance and hours of use, from the sleep apnea treatment equipment to the general coordinator 137.

The operator of a transport vehicle may initially utilize wireless transmission technology to transmit sleep apnea treatment equipment data to the general coordinator.

The wireless transmission of data from the monitoring equipment's compliance chip to the general coordinator can utilize a beeper data transfer system, a cell phone data transfer system, or a satellite wireless data transfer system.

The method further involves the general coordinator contacting each operator of a transport vehicle with sleep apnea for a first predetermined period of continuous compliance monitoring 139, such as within the first 72 hours of treatment initiation, to additionally evaluate sleep apnea treatment equipment performance and operator CPAP machine comfort and compliance. Sleep apnea treatment equipment performance data can include number of hours and days of usage of the CPAP machine, mask leak quantification, and apnea index, which is the number of times the operator's throat closes off during CPAP machine treatment.

Following a first predetermined period, the general coordinator periodically contacts 141 each operator of a transport vehicle being treated. For example, the general coordinator can periodically contact the operators of transport vehicles with sleep apnea for about two to about eight weeks by phone to ascertain sleep apnea treatment equipment performance and the operator CPAP machine comfort and compliance. The periodic contacting could be by the general coordinator or a designate of the general coordinator contacting the operator once a week. The periodic contacting can take place during a second predetermined time of continuous compliance monitoring.

After the second predetermined time of continuous compliance monitoring, such as about 15 to about 60 days, each operator being treated returns the data transfer device to the general coordinator 143.

If the equipment is not returned, the general coordinator or a designate of the general coordinator continues to track sleep apnea treatment equipment data for each of the operators as step 145.

The general coordinator or designate can continue to track sleep apnea treatment equipment data for each of the operators of the transport vehicles with sleep apnea by requesting the operator to periodically download the CPAP machine's compliance chip data onto a portable memory card.

The operators with sleep apnea can download the sleep apnea treatment equipment data to an encrypted removable data storage device 147. The encrypted removable data storage device can be a data card or other flash memory device.

The general coordinator or a designee of the general coordinator performs the step of transferring sleep apnea treatment equipment data from the encrypted removable data storage device to a processor 149.

The processor can be a personal computer, a wearable computer, a hand-held computer, a lap top computer, or a similar device, such as a cellular telephone with advanced memory capability.

The general coordinator compiles the sleep apnea treatment equipment data using the processor to create a compliance report 151. The compliance report can include information such as, an average number of hours per night the operator used his CPAP machine.

FIG. 2 is an embodiment of the system 11 that can be used with embodiments of the method for operators of transport vehicles to input data into a sleep apnea screening questionnaire.

The FIG. 2 system 11 includes a server 13, such as a processor associated with data storage having an input device and an output device with the computer instructions resident in the data storage.

The server 13 is depicted connected to an input device 15, which can be a keyboard, a tactile display screen, an audio input device with voice recognition software, a cellular device, or similar devices.

The server 13 is also connected to an output device 17, such as a microphone using text to speech software, a digital monitor, a cellular telephone, a printer, a computer, or combinations thereof.

The server 13 is connected to data storage 19, such as a memory card, a flash drive, or a similar memory device. The data storage 19 contains a plurality of secure computer instructions. For example, the data storage 19 can include operating code 23, computer instructions for playing the sleep apnea diagnostic screening questionnaire 25, computer instructions for performing an odds ratio and/or a linear regression model 29 on the answers to the diagnostic screening questionnaire, and computer instructions for compiling data 27.

The server 13 is in encrypted communication with a network 31, such as the internet, a local area network, a wide area network, a virtual private network, a cellular network, a fiber optic network, or other similar networks. The network 31 is in encrypted communication with at least one client device 33, such as a personal computer.

In an embodiment, the computer instructions can further include a dataset using outcomes from at least 500 operators of transport vehicles. The dataset can be used to form a useable linear regression model for determining positive predictive values for sleep apnea.

After the linear regression model is applied, an odds ratio model can be first utilized in determining risk stratification for sleep apnea in all groups. Individual odds ratios can be assigned to specific health conditions and specific symptoms based on results from published medical research. These odds ratios can be modified based on outcome data available on 115 operator of a transport vehicles tested for sleep apnea. A composite odds ratio value can be calculated as the product of all individual odds ratios.

Retrospective analysis of 115 operators of a transport vehicles tested for sleep apnea demonstrated that a composite odds ratio of 8.0 or greater for males, and 1.9 or greater for females, of Witnessed Apnea Negative WA−) and Excessive Daytime Sleepiness Negative EDS−) would generate a high positive predictive value of at least 85%.

A subsequent analysis of over 500 additional operators of a transport vehicles tested for sleep apnea confirmed an 88 percent positive predictive value for these groups from the odds ratio model applied after the linear regression model is applied.

A retrospective analysis of 115 operators tested for sleep apnea demonstrated that the presence of witnessed apnea WA+) was highly predictive for sleep apnea. For this reason, all operators reporting witnessed apnea were considered at high risk for sleep apnea. A subsequent analysis of over an additional 500 operators of transport vehicles tested for sleep apnea confirmed a 90 percent positive predictive value for this single risk factor.

Subsequent analysis of 500 more operators confirmed the aforementioned statistical model is capable of a greater than 85 percent positive predictive value for sleep apnea in all groups except for male Excessive Daytime Sleepiness Positive+), Witnessed Apnea−). For this group, linear regression is applied following a composite odds ratio calculation.

To generate the linear regression model for all male users indicating a positive response for excessive daytime sleepiness EDS+), witnessed apnea negative WA−), a model was created by exploring all possible models with main effects and pair-wise interactions with the following variables: body mass index, age, hypertension, diabetes, heartburn, heart condition, snoring, asthma, depression, frequent urination at night, and painful sleep.

The "best" model was chosen by using both forward and backward selection using the AIC criterion (the function step in R). After selecting this model, subjects were assigned a probability of apnea inverse log odds of linear combination. Using the usual 0.5 cutoff on the estimated probability, a cross-validated positive-predictive value of 0.876 was achieved. To get to the goal of 0.88, a cutoff of 0.65 was preferred. This calculation gave an estimated 0.891 percent positive predictive value using cross-validation.

FIG. 3 shows an exemplary health screening survey requesting company personal information and individual personal information.

Company information includes a name of a company 100, such as Precision Pulmonary Diagnostics, an operator number 102, such as 12468, a classification code 104, such as a standby pilot, a location 106, such as Houston Operating Center, and a date of hire 108, such as Feb. 13, 2007.

Personal information that a user may input includes a last name 110, a first name 112, a middle initial 114, a date of birth 116, a social security number 118, gender, 120, height 122, and weight 124. Other information that is not depicted but can be entered can include: smoking history, a history of nasal conditions, a history of sinus conditions, or other indications of other health conditions, such as hypertension or diabetes.

FIG. 4 depicts an exemplary sleep apnea diagnostic questionnaire requesting health information such as health conditions, personal symptoms, prior operations, and medications.

Some questions of the survey include: Do you have high blood pressure? 134, Do you have diabetes? 136, Have you been treated for heartburn? 138, Do you have heart problems? 140, Have you ever undergone a heart operation or procedure? 142, Do you take any of the following medications: isorbide dinitrate, such as Isordil™ or Ismo™, nitroglycerin, amiodarone, such as Cardarone™? 144, Do you have sleep apnea? 146, Do you take any of the following medications: metformin, such as Glucophage™, glyburide, such as Glucotrol™, Actos™, or Avandia™, or any other diabetes medications? 148, Do you have COPD (emphysema)? 150, Do you have asthma? 152, Have you been treated for depression? 154), Do you snore louder than talking? 156, Does your snoring bother other people? 158, Do you take any of the following medications: Plavix™, Trental™, or Persantine™? 160, Do you take any of the following medications: Protonix™, Prevacid™, Nexium™, Pepcid™, or Tagamet™? 162, On average, do you urinate more than once per night? 164, Do you become drowsy while driving? 166, Does head, back, neck, or joint pain affect your sleeping? 168, Do you take any of the following medications: enalapril, such as Vasotec™, Cozar™, Lotril™, Norvasc™, lisinopril, hydrochlorthiazide, or furosemide, such as Lasix™? 169, Do you take ANY of the following medications: Inderal™, Toprol™, Metoprolol™, Coreg™, or Lopressor™? 170, Do you take ANY of the following medications: Digoxin™, Coumadin™? 172, Do you sleep restlessly or find the blankets on the floor in the morning? 174, Has anyone noticed that you quit breathing during your sleep? 176. Have you awakened from sleep with gasping breaths? 178.

FIG. 5 shows an example health screening survey requesting situational answers from a situational questionnaire. The questions ask operators to input their chance of dozing while performing certain tasks. Typical questions include: Do you doze while: Sitting and reading 180?, Watching TV 182?, Sitting inactive in a public place 184?, Sitting as a passenger in a car for an hour without a break 186?. Questions include Do you fall asleep while: Lying down to rest anytime circumstances permit 188?, Sitting and talking to someone 190?, Sitting quietly after lunch without alcohol 192?, In a truck or car, while stopping for a few minutes in traffic 194?. FIG. 4 can also include a question requesting a male user to input his neck size 195.

FIG. 6 shows an example of a thank you screen that is shown to the operator after completing the health screening survey 196 which ensures each question is answered.

In an embodiment, the screen depicted in FIG. 5 can also include an electronic copy of an operator's responses to the web based questionnaire for the operator's records. It can also be contemplated that an acknowledgement or verification, such as an e-mail, is sent and could include this survey information.

FIG. 7 shows an example screen of survey rankings, rankings that enable an administrator to view multiple users simultaneously after each had completed the sleep apnea diagnostic screening questionnaire.

Respondents are split between male and female respondents. In addition, respondents are separated into three different categories based upon the presence or absence of witnessed apneas and the presence or absence of excessive daytime sleepiness determined by each operator's input information and questionnaire responses. The three categories are witnessed apnea positive (WA+) 198, witnessed apnea negative 199 and excessive daytime sleepiness positive (WA−/EDS+), and witnessed apnea negative and excessive daytime sleepiness negative (WA−/EDS−) 200. The witnessed apnea positive 198, the witnessed apnea negative and excessive daytime sleepiness positive 199, and witnessed apnea negative and excessive daytime sleepiness negative 200 categories list the number of male and female operators which relate to each category. Individual operators can be located as well by their social security number 206, operator number 208, and last name 210.

FIG. 8 shows exemplary survey rankings enabling a general coordinator to select an operator of a transport vehicle and view his/her status of whether or not they had been contacted and other pertinent information. Operators of a transport vehicles would be listed with information showing their name 212, social security number 214, location 216, operator number 218, gender 220, presence or absence of witnessed apnea 225, risk rating for sleep apnea 224, whether or not they have responded positively to a question asking whether they have sleep apnea, notated as alert 226, date of entry 228, date of hire 229, and status of contacting, scheduling, and testing the operator of a transport vehicle 230.

The status of contacting the operator of a transport vehicle 230 can include an indication that the operator of a transport vehicle has been referred 231, an indication that the operator of a transport vehicle has been contacted 233, an indication that the operator of a transport vehicle has been scheduled for a sleep study 235, and an indication that the operator of a transport vehicle has completed a sleep study 237. Additional ways that an operator of a transport vehicle can be listed can include additional fields and columns tailored to the needs of a company needing the study results.

FIG. 9A shows a screen of an operator after an administrator selected the operator and the answers to the health screening questions. Individual information of the operator is shown including the name 232, social security number 234, location 236, driver number 238, gender 240, presence or absence of witnessed apnea 244, presence or absence of excessive daytime sleepiness 245, a probability score 246, and whether or not the operator has been flagged for a sleep apnea follow-up 248.

It should be noted in FIG. 9A that change buttons 249, can be included which allow a general coordinator or similar administrator to change or correct personal and company information, such as when an operator makes a typographical error.

FIG. 9A includes a comment section 251, which allows one or more general coordinators or similar administrators to enter comments regarding a specific operator or specific operator information, such as how an operator was referred to the study, pertinent information regarding the operator's medical history, and other information.

FIG. 9B shows a screen of an operator after an administrator selected the operator with a complete list of the operator's survey responses 250.

FIG. 9C depicts a screening history 253 for the operator. Additional individual information of the operator can be shown including an indication of smoking history, a history of nasal or sinus conditions, or other health information or information regarding medical conditions or medical history.

FIG. 10 shows the abilities of a general coordinator or similar administrator to sort and filter different operators that are in the database. Different filters that a general coordinator or similar administrator can utilize include classifications 252, locations 254, and treatment facilities 256, which can be any testing facility where a sleep test is performed. A general coordinator or similar administrator can use one or more sort menus 258, and sort by categories such as probability and status. Additional filters or sort menus that can be used include a filter or sort menu relating to administrative status, a filter relating to whether an operator is experienced, or a filter relating to date of entry or date of hire.

While these embodiments have been described with emphasis on the embodiments, it should be understood that within the scope of the appended claims, the embodiments might be practiced other than as specifically described herein.

What is claimed is:

1. A method for delivering sleep apnea screening, sleep apnea treatment, and sleep apnea treatment compliance monitoring on an at least one operator of a transport vehicle of a transport company by a general coordinator comprising:
   a. the sleep apnea screening comprising:
      i. providing input information to the general coordinator using a secured sleep apnea diagnostic screening questionnaire completed by the at least one operator of a transport vehicle;
      ii. determining positive predictive values for sleep apnea by categorizing input information using computer instructions on a server to categorize the input information into a member of the group consisting of: male Witnessed Apnea Positive (WA+), female Witnessed Apnea Positive (WA+), male Witnessed Apnea Negative (WA−) and Excessive Daytime Sleepiness Positive (EDS+) requiring an odds ratio calculation, female Witnessed Apnea Negative (WA−) and Excessive Daytime Sleepiness Positive (EDS+) requiring an odds ratio calculation, male Witnessed Apnea Negative (WA−) and Excessive Daytime Sleepiness Negative (EDS) requiring an odds ratio calculation, or female Witnessed Apnea Negative (WA−) and Excessive Daytime Sleepiness Negative (EDS−) requiring an odds ratio calculation;

iii. providing a health screening service report using the categorized input information from the general coordinator to the transport company adapted to identify operators of transport vehicles with high predictive values for sleep apnea;

iv. providing a summary of all positive predictive values using input information to the transport company; and b. the sleep apnea treatment comprising:

i. directing at least one operator of a transport vehicle to a physician to prescribe a sleep test for sleep apnea and transmitting the results of the sleep test to the general coordinator; and ii. providing sleep apnea treatment equipment comprising a data transfer device paired with a CPAP machine comprising a compliance chip by the general coordinator to each operator of a transport vehicle indicated by the sleep apnea test data to have sleep apnea simultaneously when the sleep apnea sleep test concludes;

c. the sleep apnea treatment compliance monitoring comprising:

i. using the data transfer device by each operator of a transport vehicle to transmit sleep apnea treatment equipment data from the sleep apnea treatment equipment to the general coordinator;

ii. contacting each operator of a transport vehicle with sleep apnea by the general coordinator after a first predetermined period of continuous compliance monitoring to ascertain sleep apnea treatment equipment performance; and iii. following the first predetermined period of contacting of each operator of a transport vehicle with sleep apnea periodically by the general coordinator to ascertain sleep apnea treatment equipment performance.

2. The method of claim 1, wherein after the first predetermined period the method further comprises the step of:

a. continuing to track sleep apnea treatment equipment data for each of the at least one operator of a transport vehicles with sleep apnea by the general coordinator for a second predetermined period of continuous compliance monitoring;

b. downloading sleep apnea treatment equipment data by each operator of a transport vehicle with sleep apnea to an encrypted removable data storage device;

c. transferring sleep apnea treatment equipment data from the encrypted removable data storage device to a processor by the general coordinator; and d. compiling the sleep apnea treatment equipment data using the processor to create a compliance report.

3. The method of claim 2, wherein the data transfer device is adapted for use with a data transfer system.

4. The method of claim 3, further comprising transmitting sleep apnea treatment equipment data from the sleep apnea treatment equipment to the general coordinator using the data transfer system.

5. The method of claim 2, further comprising the step of continuing to track sleep apnea treatment equipment data for each operator of a transport vehicle while complying with specified requirements established by the transport company after the second predetermined time of continuous compliance monitoring by the general coordinator.

6. The method of claim 5, wherein the second predetermined time of continuous compliance monitoring is between 2 weeks to 4 weeks.

7. The method of claim 2, wherein the encrypted removable data storage device comprises flash memory cards, flash drives, portable hard drives, memory cards, modems, and direct cable connections to the processor.

8. The method of claim 2, further comprising providing the compliance report for the at least one operator of a transport vehicle with sleep apnea to the transport company by the general coordinator.

9. The method of claim 2, further comprising associating the compliance report and the health screening service report by the general coordinator with each operator of a transport vehicle.

10. The method of claim 1, wherein the input information to the general coordinator further comprises providing answers to the secure sleep apnea screening questionnaire to the general coordinator by each operator of a transport vehicle using a client device connected in encrypted communication with a network further in communication with at least one server; and wherein the at least one server communicates with an input device, an output device, and a data storage, wherein the data storage comprises encrypted computer instructions for the sleep apnea screening questionnaire, and encrypted computer instructions providing a confirmation e-mail to the at least one operator of a transport vehicle by the server.

11. The method of claim 1, wherein the sleep apnea treatment equipment data provides hours of use, data on mask leakage, and an apnea index based on throat closure during sleep apnea treatment compliance monitoring.

12. The method of claim 1, further comprising providing delivery of sleep apnea screening, sleep apnea treatment, and sleep apnea treatment compliance monitoring simultaneously on a plurality of operators of transport vehicles simultaneously to a plurality of transport companies.

13. The method of claim 1, wherein the method is complaint with the United States Health Insurance Portability and Accountability Act of 2002, 42 C.F.R. section 164.

14. The method of claim 1, further comprising providing an individualized health screening service report to the at least one operator of a transport vehicle.

15. The method of claim 14, further comprising providing the individualized health screening service report by e-mail.

16. The method of claim 1, wherein the individual personal information comprises:

a. name of an operator;
b. an employee number for each operator;
c. gender for each operator;
d. social security number for each operator;
e. an alert icon for self admitted sleep apnea;
f. date of input of information;
g. date of hire; or
h. at least one company designated field.

17. The method of claim 1, further comprising compiling the results of the sleep apnea sleep test with the categorized input information to provide a summary of data of the sleep apnea sleep test administered operators of transport vehicles of a commercial transport company with the categorized input information.

18. The method of claim 1, capable of generating a health screening survey report for the company comprising a member of the group comprising of:

a. company name;
b. gender of operator;
c. presence of absence of sleep apnea;
d. body mass index;
e. an indication of hypertension;
f. an indication of diabetes;
g. an indication of heart disease;
h. an operator's neck size range;
i. an indication of lung disease;

j. an indication of asthma;
k. an indication of heart burn;
l. an indication of frequent urination at night; and
m. combinations thereof.

19. The method of claim 1, further comprising flagging at least operator with self admitted sleep apnea for additional validation data supporting self admitted sleep apnea.

20. The method of claim 1, wherein the health screening service report comprises a look-up table for each operator by name, employee number, or social security number.

21. The method of claim 1, further comprising creating additional reports comprising:
   a. sleep test results;
   b. compliance reports; or
   c. receipts verifying delivery of equipment.

22. The method of claim 1, further comprising confirming the company has a United States Health Insurance Portability and Accountability Act of 2002 42 CFR section 164, compliant release for each operator.

23. The method of claim 1, wherein the sleep apnea screening questionnaire comprises:
   a. company employee information;
   b. individual personal information;
   c. personal health information.

24. The method of claim 1, wherein the sleep apnea screening questionnaire further comprises a situational questionnaire with gender related questions.

25. The method of claim 1, wherein the health screening service report comprises:
   a. at least one rating per operator, wherein the rating comprises an member of the group consisting of:
   b. individualized numerical scores indicating a positive predictive value for at least one operator; and
   c. a high, medium, or low positive predictive value for at least one operator.

\* \* \* \* \*